United States Patent
Esteller et al.

(10) Patent No.: US 11,129,987 B2
(45) Date of Patent: Sep. 28, 2021

(54) ADJUSTMENT OF STIMULATION IN A STIMULATOR USING DETECTED EVOKED COMPOUND ACTION POTENTIALS

(71) Applicant: Boston Scientific Neuromodulation Corporation, Valencia, CA (US)

(72) Inventors: Rosana Esteller, Santa Clarita, CA (US); Goran N. Marnfeldt, Valencia, CA (US); Natalie A. Brill, Sherman Oaks, CA (US); David M. Wagenbach, Simi Valley, CA (US); Pujitha Weerakoon, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 166 days.

(21) Appl. No.: 16/135,961

(22) Filed: Sep. 19, 2018

(65) Prior Publication Data
US 2019/0099602 A1 Apr. 4, 2019

Related U.S. Application Data

(60) Provisional application No. 62/568,211, filed on Oct. 4, 2017.

(51) Int. Cl.
*A61N 1/36* (2006.01)
*A61N 1/372* (2006.01)
*A61N 1/05* (2006.01)

(52) U.S. Cl.
CPC ....... *A61N 1/36139* (2013.01); *A61N 1/0553* (2013.01); *A61N 1/36062* (2017.08);
(Continued)

(58) Field of Classification Search
USPC .......................................... 607/62
See application file for complete search history.

(56) References Cited

U.S. PATENT DOCUMENTS

| | | |
|---|---|---|
| 5,697,958 A | 12/1997 | Paul et al. |
| 5,702,429 A | 12/1997 | King |

(Continued)

FOREIGN PATENT DOCUMENTS

| | | |
|---|---|---|
| EP | 2709721 | 9/2016 |
| WO | 2006/029090 | 3/2006 |

(Continued)

OTHER PUBLICATIONS

International Search Report and Written Opinion regarding corresponding PCT Application No. PCT/US2018/051783, dated Dec. 20, 2018.

(Continued)

*Primary Examiner* — Nicole F Lavert
(74) *Attorney, Agent, or Firm* — Lewis & Reese, PLLC

(57) ABSTRACT

An Implantable Pulse Generator (IPG) or External Trial Stimulator (ETS) system is disclosed that is capable of sensing an Evoked Compound Action Potential (ECAP), and (perhaps in conjunction with an external device) is capable of adjusting a stimulation program while keeping a location of a Central Point of Stimulation (CPS) constant. Specifically, one or more features of measured ECAP(s) indicative of its shape and size are determined, and compared to thresholds or ranges to modify the electrode configuration of the stimulation program.

20 Claims, 11 Drawing Sheets

(52) U.S. Cl.
CPC ..... *A61N 1/36171* (2013.01); *A61N 1/36175* (2013.01); *A61N 1/36185* (2013.01); *A61N 1/37241* (2013.01)

(56) References Cited

U.S. PATENT DOCUMENTS

| | | | |
|---|---|---|---|
| 5,814,092 | A | 9/1998 | King |
| 5,902,236 | A | 5/1999 | Iversen |
| 5,902,249 | A | 5/1999 | Lyster |
| 5,913,882 | A | 6/1999 | King |
| 6,078,838 | A | 6/2000 | Rubenstein |
| 6,181,969 | B1 | 1/2001 | Gord et al. |
| 6,516,227 | B1 | 2/2003 | Meadows et al. |
| 6,907,130 | B1 | 6/2005 | Rubernstein |
| 7,024,247 | B2 | 4/2006 | Gliner et al. |
| 7,424,322 | B2 | 9/2008 | Lombardi et al. |
| 7,450,992 | B1 | 11/2008 | Cameron |
| 8,255,057 | B2 | 8/2012 | Fang et al. |
| 8,335,664 | B2 | 12/2012 | Eberle |
| 8,352,030 | B2 | 1/2013 | Denison |
| 8,412,345 | B2 | 4/2013 | Moffitt |
| 8,463,400 | B2 | 6/2013 | Hegi et al. |
| 8,594,797 | B2 | 11/2013 | Lee |
| 8,606,362 | B2 | 12/2013 | He et al. |
| 8,620,436 | B2 | 12/2013 | Parramon et al. |
| 8,768,453 | B2 | 7/2014 | Parramon et al. |
| 8,825,169 | B2 | 9/2014 | Zhu et al. |
| 8,909,350 | B2 | 12/2014 | Lee |
| 8,913,804 | B2 | 12/2014 | Blum et al. |
| 9,014,820 | B2 | 4/2015 | Lee et al. |
| 9,044,155 | B2 | 6/2015 | Strahl |
| 9,061,140 | B2 | 6/2015 | Shi et al. |
| 9,119,964 | B2 | 9/2015 | Marnfeldt |
| 9,149,636 | B2 | 10/2015 | Moffitt et al. |
| 9,155,892 | B2 | 10/2015 | Parker et al. |
| 9,248,274 | B2 | 2/2016 | Troosters et al. |
| 9,248,279 | B2 | 2/2016 | Chen et al. |
| 9,265,431 | B2 | 2/2016 | Hincapie Ordonez et al. |
| 9,302,112 | B2 | 4/2016 | Bornzin et al. |
| 9,381,356 | B2 | 7/2016 | Parker et al. |
| 9,386,934 | B2 | 7/2016 | Parker et al. |
| 9,387,334 | B2 | 7/2016 | Lee et al. |
| 9,403,013 | B2 | 8/2016 | Walker et al. |
| 9,409,020 | B2 | 8/2016 | Parker |
| 9,526,897 | B2 | 12/2016 | Chen et al. |
| 9,533,148 | B2 | 1/2017 | Carcieri et al. |
| 9,731,116 | B2 | 8/2017 | Chen |
| 9,872,990 | B2 | 1/2018 | Parker et al. |
| 9,974,455 | B2 | 5/2018 | Parker et al. |
| 10,076,667 | B2 | 9/2018 | Kaula et al. |
| 2002/0156513 | A1 | 10/2002 | Borkan |
| 2005/0246004 | A1 | 11/2005 | Cameron et al. |
| 2008/0146894 | A1 | 6/2008 | Bulkes et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2012/0116475 | A1 | 5/2012 | Nelson et al. |
| 2013/0035745 | A1* | 2/2013 | Ahmed ............. A61N 1/36103 607/66 |
| 2013/0053926 | A1* | 2/2013 | Hincapie ............ A61N 1/36114 607/62 |
| 2013/0289665 | A1 | 10/2013 | Marnfeldt et al. |
| 2014/0100632 | A1 | 4/2014 | Rao et al. |
| 2014/0180361 | A1* | 6/2014 | Burdick ............. A61N 1/36007 607/49 |
| 2014/0194772 | A1 | 7/2014 | Single et al. |
| 2014/0236042 | A1 | 8/2014 | Parker et al. |
| 2014/0296737 | A1 | 10/2014 | Parker et al. |
| 2015/0018898 | A1 | 1/2015 | Tass |
| 2015/0032181 | A1 | 1/2015 | Baynham et al. |
| 2015/0080982 | A1 | 3/2015 | Funderburk |
| 2015/0157861 | A1 | 6/2015 | Aghassian et al. |
| 2015/0246230 | A1 | 9/2015 | Litvak |
| 2015/0282725 | A1 | 10/2015 | Single et al. |
| 2015/0313487 | A1 | 11/2015 | Single et al. |
| 2015/0360038 | A1 | 12/2015 | Zottola et al. |
| 2015/0374999 | A1 | 12/2015 | Parker et al. |
| 2016/0166164 | A1 | 6/2016 | Obradovic et al. |
| 2016/0287126 | A1 | 10/2016 | Parker et al. |
| 2016/0287182 | A1 | 10/2016 | Single et al. |
| 2016/0303368 | A1 | 10/2016 | Parramon et al. |
| 2017/0049345 | A1 | 2/2017 | Single et al. |
| 2017/0071490 | A1 | 3/2017 | Parker et al. |
| 2017/0135624 | A1 | 5/2017 | Parker et al. |
| 2017/0216587 | A1 | 8/2017 | Parker et al. |
| 2017/0281958 | A1 | 10/2017 | Serrano Carmona et al. |
| 2017/0296823 | A1 | 10/2017 | Hershey et al. |
| 2017/0361101 | A1 | 12/2017 | Single et al. |
| 2018/0056068 | A1 | 3/2018 | Zhang et al. |
| 2018/0071520 | A1 | 3/2018 | Weerakoon et al. |
| 2018/0071527 | A1 | 3/2018 | Feldman et al. |
| 2018/0110987 | A1 | 4/2018 | Parker et al. |
| 2018/0117335 | A1 | 5/2018 | Parker et al. |
| 2018/0132747 | A1 | 5/2018 | Parker et al. |
| 2018/0132760 | A1 | 5/2018 | Parker et al. |
| 2018/0133459 | A1 | 5/2018 | Parker et al. |
| 2018/0140831 | A1 | 5/2018 | Feldman et al. |
| 2018/0228391 | A1 | 8/2018 | Parker et al. |
| 2018/0228547 | A1 | 8/2018 | Parker et al. |
| 2018/0256052 | A1 | 9/2018 | Parker et al. |
| 2019/0099602 | A1 | 4/2019 | Esteller et al. |

FOREIGN PATENT DOCUMENTS

| | | |
|---|---|---|
| WO | 2015/077362 A1 | 5/2015 |
| WO | 2017/100866 | 6/2017 |
| WO | 2017/173493 | 10/2017 |
| WO | 2017/210352 A1 | 12/2017 |
| WO | 2017/219096 | 12/2017 |

OTHER PUBLICATIONS

Precision Spectra™ System Programming Manual, Boston Scientific Corp., 90834018-18 Rev A (2016).
E. Viezi et al., "Spinal Cord Stimulation (SCS) with Anatomically Guided (3D) Neural Targeting Shows Superior Chronic Axial Low Back Pain Relief Compared to Traditional SCS—LUMINA Study," Pain Medicine, pp. 1-15 (2017).
J. Parker et al., "Electrically Evoked Compound Action Potential Recorded From the Sheep Spinal Cord", Neuromodulation, 16:295-303 (2013).
J. Parker, et al., "Compound Action Potentials Recorded in Human Spinal Cord During Neurostimulation for Pain Relief," PAIN, vol. 153(3), pp. 593-601 (Mar. 2012).
W.D. Willis, Jr. et al., "Sensory Mechanisms of the Spinal Cord: Volume 2 Ascending Sensory Tracts and Their Descending Control: Third Edition," Springer Science & Business Media, Chap. 7, p. 278 (2013).
M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).
I. Akhoun et al., "Electrically evoked compound action potential artifact rejection by independent component analysis: Technique validation," Hearing Research 302 pp. 60-73 (2013).
M. Moffit et al., A Novel 3-Dimensional Algorithm for Model-Based Programming in Spinal Cord Stimuation (SCS): Illumina-3D™, presentation (2013).
T. Kano et al., "Evoked Spinal Cord Potentials: An Illustrated Guide to Physiology, Pharmacology, and Recording Techniques," To Print ISBN 978-4-431-24026-6, Chapter 4, pp. 40-49 (2006).
U.S. Appl. No. 62/641,748, Zhu et al.
U.S. Appl. No. 62/648,231, Esteller et al.
U.S. Appl. No. 62/650,844, Marnfeldt et al.
U.S. Appl. No. 62/679,259, Esteller et al.
U.S. Appl. No. 62/768,617, Esteller et al.
U.S. Appl. No. 62/825,982, Wagenbach et al.
U.S. Appl. No. 16/210,794, Brill et al.
U.S. Appl. No. 16/238,151, Esteller et al.

(56) References Cited

OTHER PUBLICATIONS

H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).
J. Rubinstein et al., "Pseudospontaneous activity: stochastic independence of auditory nerve fibers with electrical stimulation," Hear Res., 127(1-2), pp. 108-118 (1999) (abstract only).
J. Paz, "Physiological Midline Mapping Based on Spinal Cord Stimulation (SCS) Response Using the 32-Contact Paddle Lead," 19$^{th}$ NANS Annual Meeting (Dec. 13-15, 2015).
E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

\* cited by examiner

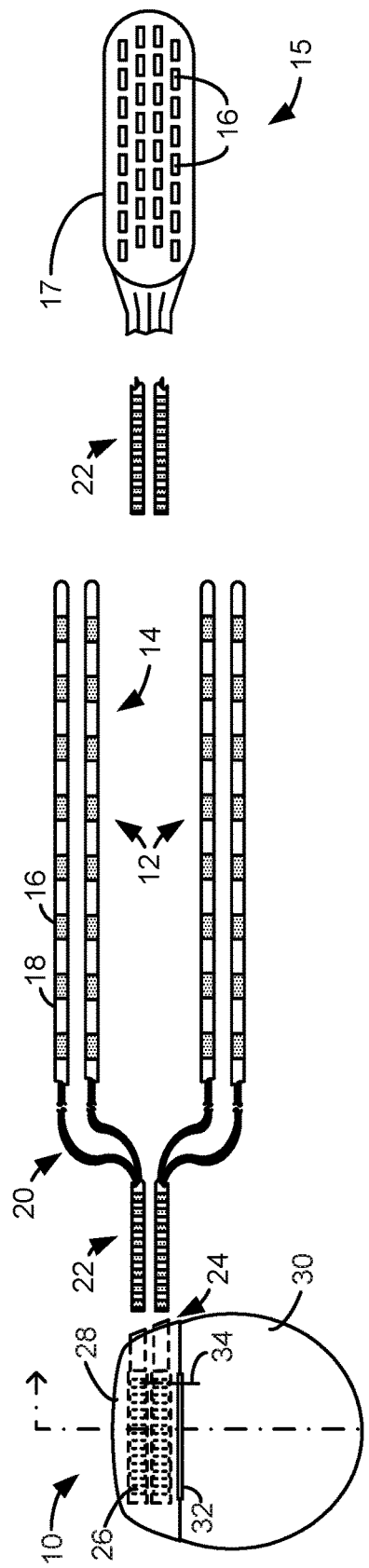
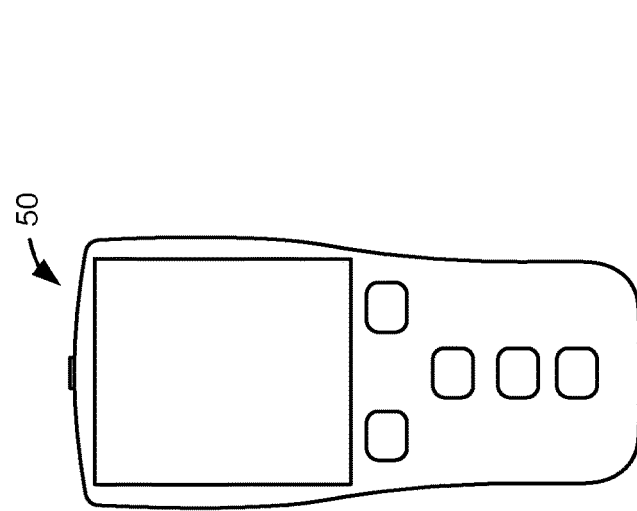
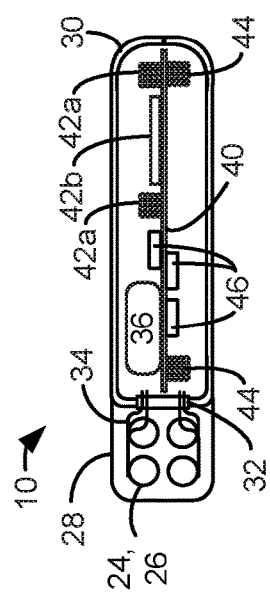
Figure 1A (prior art)
Figure 1B (prior art)
Figure 2 (prior art)

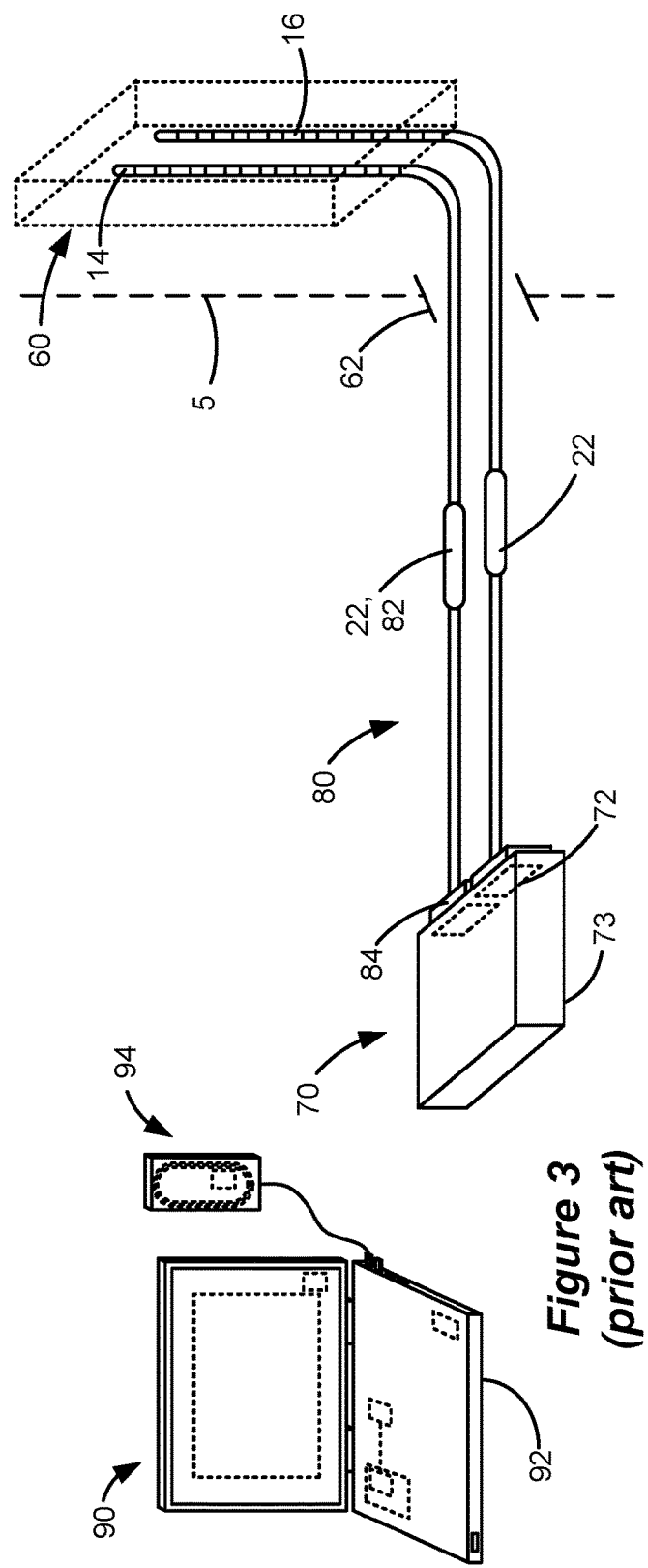
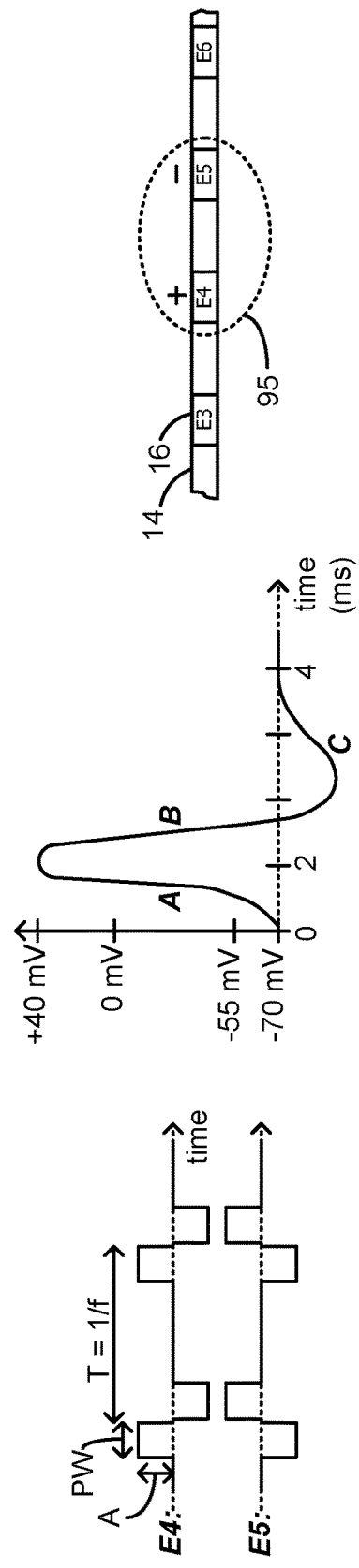
*Figure 3 (prior art)*
*Figure 4 (prior art)*
*Figure 5 (prior art)*
*Figure 6 (prior art)*

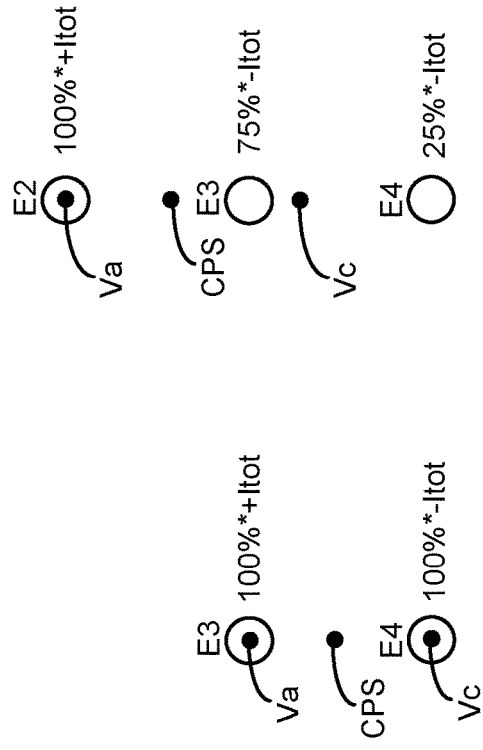
Figure 10A
Figure 10B
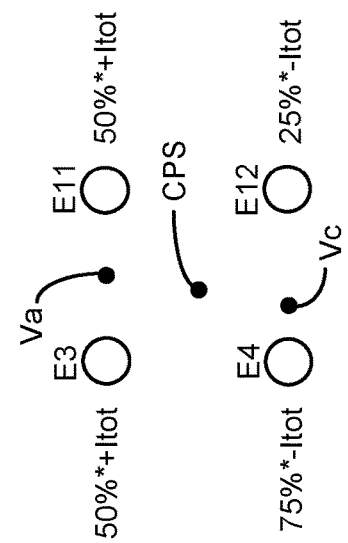
Figure 10C
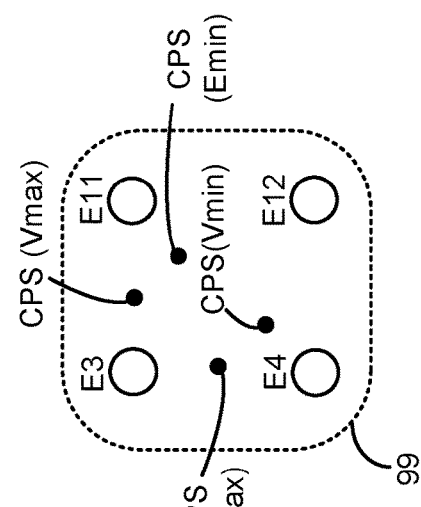
Figure 10D
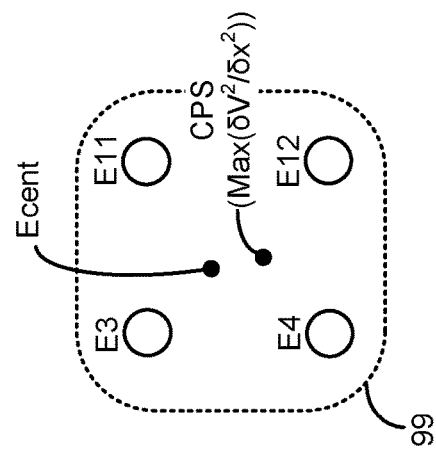
Figure 10E

ADJUSTMENT OF STIMULATION IN A STIMULATOR USING DETECTED EVOKED COMPOUND ACTION POTENTIALS

CROSS REFERENCE TO RELATED APPLICATIONS

This is a non-provisional application of U.S. Provisional Patent Application Ser. No. 62/568,211, filed Oct. 4, 2017, which is incorporated herein by reference in its entirety, and to which priority is claimed.

FIELD OF THE INVENTION

The present invention relates generally to medical device systems, and more particularly to pulse generator systems operable to measure an Evoked Compound Action Potential (ECAP) that can be used to adjust stimulation therapy.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat different neurological conditions including movement disorders, psychological disorders, migraine disorders, and epilepsy among others, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14, with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. Two 16-electrode leads could also be used with each having a splitter allowing the leads to be connected to two lead connectors 24. Each of the IPG's lead connectors 24 can also support for example 12 or 16 electrodes. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; and a charging coil 44 for wirelessly receiving a magnetic charging field from an external charger (not shown) for recharging the battery 36. If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2), or a clinician programmer 90 (FIG. 3). Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS).

Implantation of IPG 10 in a patient is normally a multi-step process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure. By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined as effective during the trial stimulation phase, it/they can then be programmed into the IPG 10, and thereafter modified wirelessly, using either the external programmer 50 or the clinician programmer 90.

An example of stimulation pulses as prescribed by a particular stimulation program and as executable by the IPG or ETS 70 is illustrated in FIG. 4. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses—having only a first pulse phase but not followed by an active-charge recovery second pulse phase—can also be used.

Biphasic pulses are useful because the second pulse phase can actively recover any charge build up after the first pulse phase residing on capacitances (such as the DC-blocking capacitors 107 discussed later with respect to FIG. 7) in the current paths between the active electrodes. In the example stimulation program shown in FIG. 4, electrode E4 is selected as the anode electrode while electrode E5 is selected as the cathode electrode (during the first pulse phase), which because two electrodes 16 are implicated, comprises what is known is bipolar stimulation. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

The stimulation program executed by the IPG 10 and ETS 70 can be set or adjusted via a communication link from the external controller (FIG. 2) or clinician programmer 90 (FIG. 3). While the external controller 50's antenna is usually within its housing, the clinician programmer 90 may include communication head or wand 94 containing an antenna and wired to computer 92. Further details concerning the clinician programmer 90 may be as described in U.S. Patent Application Publication 2015/0360038, and further details concerning an external controller can be found in U.S. Patent Application Publication 2015/0080982. As is known, both of the external communication devices have graphical user interfaces that can be used by the clinician or patient to set and adjust the stimulation program that the IPG 10 or ETS 70 will run.

BRIEF DESCRIPTION OF THE DRAWINGS

FIGS. 1A and 1B respectively show an Implantable Pulse Generator (IPG) in plan and cross sectional views, in accordance with the prior art.

FIG. 2 shows a hand-held external controller for communicating with an IPG, in accordance with the prior art.

FIG. 3 shows a clinician programming system for communicating with an IPG or an External Trial Stimulator (ETS), in accordance with the prior art.

FIG. 4 shows pulses in a stimulation program, in accordance with the prior art.

FIG. 5 shows a graph of an action potential of a neuron, in accordance with the prior art.

FIG. 6 shows an electromagnetic field produced in a patient's tissue for recruiting neurons to fire, in accordance with the prior art.

FIGS. 10A-10E show different manner in which CPS can be defined and calculated.

DETAILED DESCRIPTION

When a neural fiber is recruited by electrical stimulation, it will issue an action potential—that is, the neural fiber will "fire." An action potential for a typical neural fiber is shown in FIG. 5. Should electrical recruitment from electrical stimulation cause the neural fiber's resting state (e.g., −70 mV as measured from inside the cell) to exceed a threshold (e.g., −55 mV), the neural fiber will depolarize ("A"), repolarize ("B"), and hyperpolarize ("C") before coming to rest again. If electrical stimulation continues, the neural fiber will fire again at some later time. Note that the action potential does not change in magnitude for a given neural fiber. Instead, changing the strength of stimulation may affect the frequency at which action potentials are issued, and may also affect what types of neural fibers are recruited. Each neural fiber is unique in its shape and size, and thus can fire at its own inherent maximum frequency.

FIG. 6 illustrates the example of FIG. 4 in which electrodes E4 and E5 on lead 14 are used to produce pulses in a bipolar mode of stimulation, with E4 comprising an anode (+; or source of current) and E5 a cathode (−; or sink of current). Such stimulation produces an electromagnetic (EM) field in a volume 95 of the patient's tissue around the selected electrodes. Some of the neural fibers within the EM field volume 95 will be recruited and fire, particularly those proximate to the cathodic electrode E5. Hopefully the sum of the neural fibers firing within volume 95 will mask signals indicative of pain in an SCS application, thus providing the desired therapy.

Figure 7:
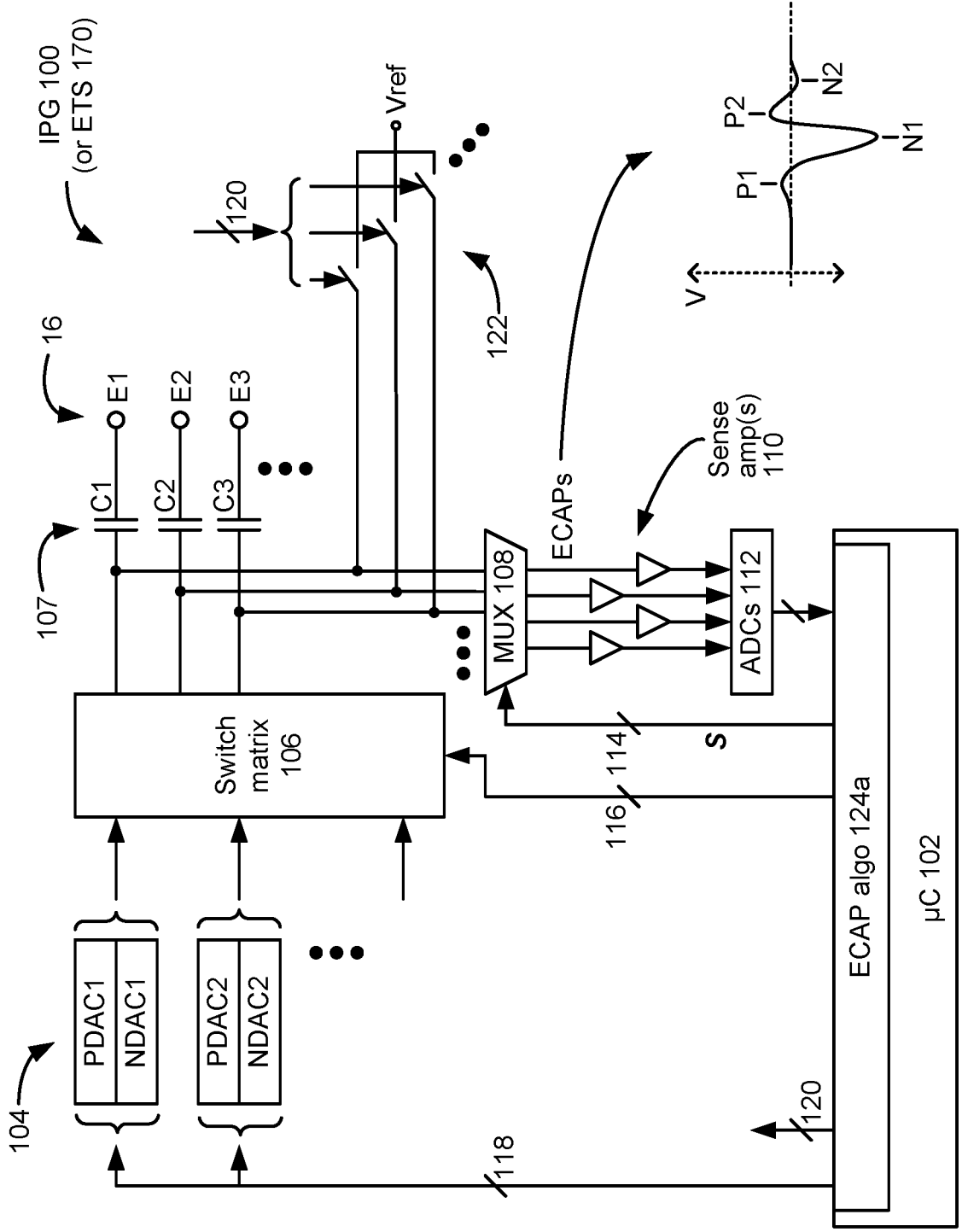
FIG. 7 shows an improved IPG (or ETS) including control circuitry programmed with an Evoked Compound Action Potential (ECAP) algorithm, and further including sensing circuitry for sensing an ECAP at a sense electrode.

Neural fibers recruited and that fire within volume 95 create a cumulative response called an Evoked Compound Action Potential, or ECAP, which is shown in FIG. 7 along with circuitry for an improved IPG 100 operable with the disclosed technique. Although described in the context of an IPG 100, it should be realized that the disclosed technique could also be operable in an improved external stimulator, such as an External Trial Stimulation 170 that generally mimics the operation of an IPG as explained earlier.

The IPG 100 (or ETS 170) includes control circuitry 102 into which an ECAP algorithm 124a can be programmed. Control circuitry 102 may comprise a microcontroller for example such as Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and U.S. Pat. Nos. 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The illustrated circuitry for producing stimulation pulses and delivering them to the electrodes is merely one example. Other approaches may be found for example in U.S. Pat. Nos. 8,606,362 and 8,620,436, and U.S. Patent Application Publication 2018/0071520. Note that a switch matrix 106 isn't required, and instead a PDAC and NDAC can be dedicated to (e.g., wired to) each electrode.

Notice that the current paths to the electrodes 16 include the DC-blocking capacitors 107 alluded to earlier, which provide additional safety by preventing the inadvertent supply of DC current to an electrode and to a patient's tissue. As discussed earlier, capacitances such as these can become charged as stimulation currents are provided, providing an impetus for the use of biphasic pulses.

One or more of the electrodes 16 can be used to sense the ECAP described earlier, and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP, described further below, is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs.

Notice that connection of the electrodes 16 to the sense amp(s) 110 preferably occurs through the DC-blocking capacitors 107, such that capacitors are between the electrodes and the sense amp(s) 110. This is preferred so as to not undermine the safety provided by the DC-blocking capacitors 107.

Figure 13:
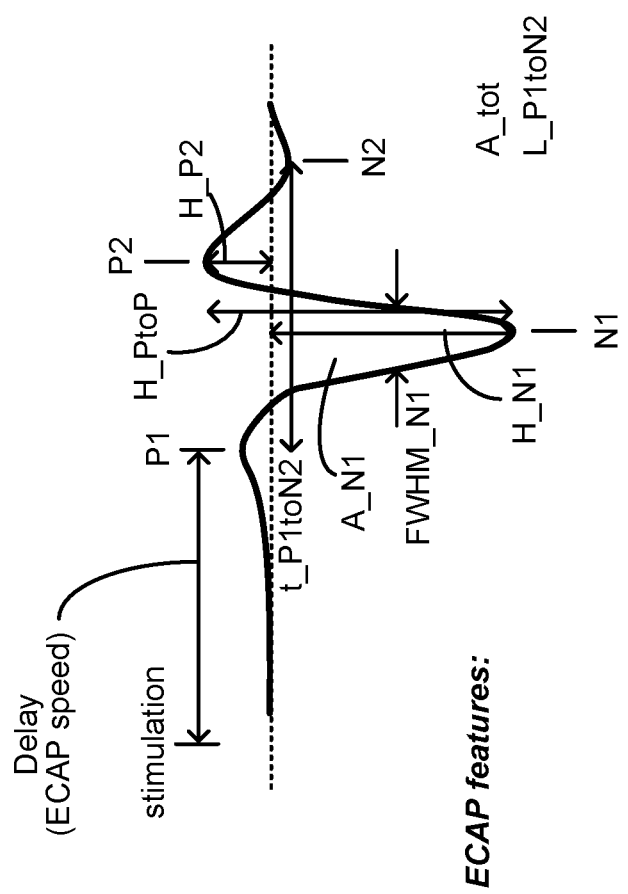
FIG. 13 shows examples of different features that can be assessed by the ECAP algorithms.

Once the digitized ECAP is received at the control circuitry 102, it is processed by the ECAP algorithm 124a to determine one or more ECAP features that describe the basic shape and size of the ECAP(s), as explained further below with reference to FIG. 13. The response to stimulation can include potentials observed at different delays corresponding to different type of neural elements recruited. The delay from the stimulus can depend on the distance between the sensed electrode and the activation region where the electrical stimulus recruited most neural elements. Neural elements include axon fibers, neuron cell bodies, neuron dendrites, axon terminals, locations where fiber collaterals branch, interneurons, glial cells, or any nervous system functional part. In the specific case of the spinal cord, the sense electrodes can be placed over the dorsal column, more laterally in the epidural space towards and over the edge of dorsal horn and/or Lissauer's tract, over the dorsal root entry zone (DREZ), the rootlets, the dorsal root ganglia (DRG), the cauda equina region, the spinal nerves close to the spinal cord, the Spino-thalamic tract, and any other of the tracts surrounding the gray matter of the spinal cord. An ECAP can contain a number of peaks or waves indicative of the different phases of the averaged or compound action potential sensed and depending on the delay with respect to the stimulus, the peak potentials can be indicative of different type of fibers activated. Axon fibers with different functions (C fibers, Aβ fibers, Aδ fibers, and others) have different diameters that correlate with different propagation velocities for the compound potentials. Conduction velocities for different axonal fiber types are known, and the conduction velocities of the ECAPs sensed in the spinal cord can be calculated to determine the originating fiber. As shown, peaks in the ECAP are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 7, because an ECAP's shape is a function of the number and types of neural fibers that are recruited in a given volume 95.

The amplitude of an ECAP will depend on how many neural fibers are firing. Generally speaking, a primary ECAP response, e.g., the height of peak N1, can vary, usually between microVolts to tens of milliVolts. Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is brought within a range that the control circuitry 102 and/or ADCs 112 can handle, such as between 3 Volts and ground.

Figure 8A:
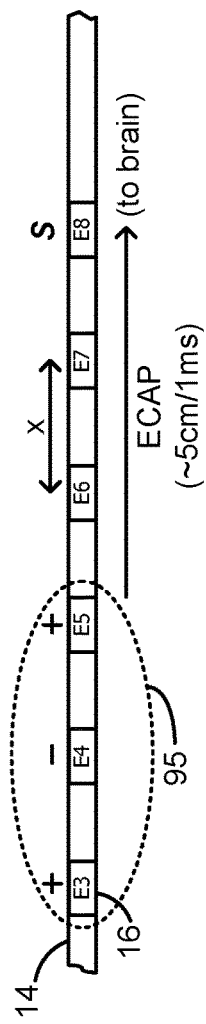
FIGS. 8A and 8B show a stimulation program, the resulting generation of an ECAP, and detection of that ECAP by the ECAP algorithm in the improved IPG (or ETS).
Figure 8B:
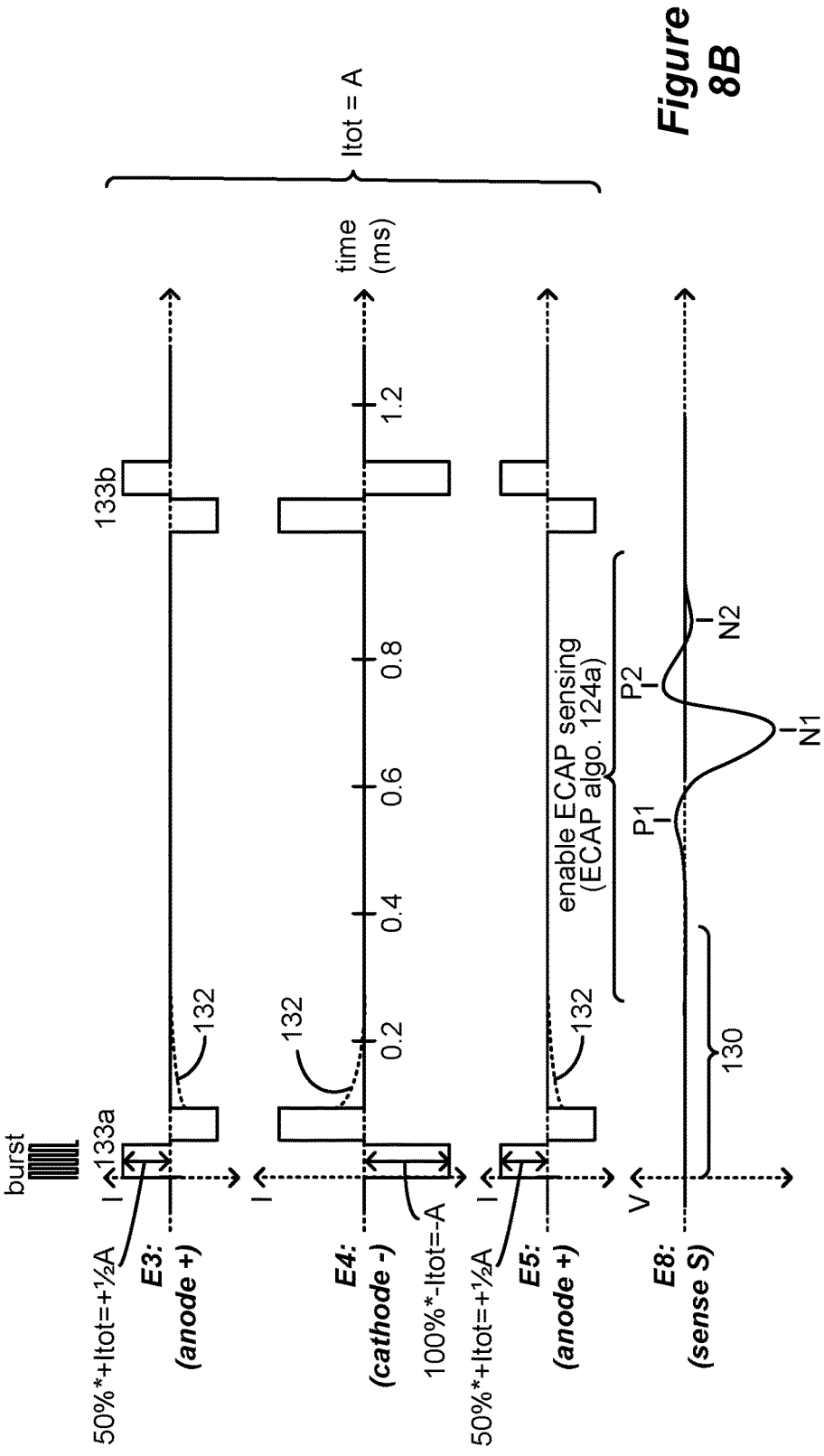

FIGS. 8A and 8B illustrate a particular stimulation program, the resulting generation of an ECAP, and detection of that ECAP. The stimulation program is defined as before by various stimulation parameters to form stimulation pulses, such as which electrodes are active for stimulation, the polarity of those electrodes, the amplitude at selected electrodes, pulse width, pulse frequency, and stimulation waveform shape (square pulses in the example shown), although these parameters are not all labeled in FIG. 8B. In the example stimulation program shown, and considering only the first phase of the biphasic pulses, electrode E4 is selected to operate as a cathode (−), and electrodes E3 and E5 are selected to operate an anodes (+). Such stimulation is usually referred to as tripolar stimulation. Tripolar stimulation is a preferred mode of providing stimulation, particularly in an SCS application, because neural fibers in the dorsal column are activated proximate to the cathode. Tripolar stimulation generally allows effective stimulation to occur at lower current amplitudes.

In the example shown, the pulses are defined with respect to a total anodic and cathodic current (collectively, Itot) that the electrodes will provide at any given time. This is desirable so that the patient's tissue will not receive a net amount of charge. The sole cathode electrode E4 provides all of the total cathodic current (−Itot), and so provides 100*−Itot, or −A. The two anode electrodes E3 and E5 must together issue the total anodic current (+Itot), and in this example each provides 50%*+Itot, or +½A. The anode electrodes can issue any anodic currents that together will equal +Itot (e.g., 70%*+Itot and 30%*+Itot. It is assumed that this particular stimulation program has been chosen as one that generally provides good therapeutic results for a particular patient.

Once stimulation begins (at time=0), an ECAP will be produced comprising the sum of the action potentials of neural fibers recruited and hence firing in volume 95. As shown in FIG. 8A, the ECAP will move through the patient's tissue via neural conduction with speeds of about 3.5-7.5 cm/ms in the typical case of Aβ fibers, or 0.3-3.0 cm/ms in the case of Aδ fibers. In the example shown, the ECAP moves to the right, which is in an orthodromic direction toward the brain (rostrally). However, the ECAP will also move in the antidromic direction as well toward the bottom of the spinal cord of the patient (caudally).

A single sense electrode (S) has been chosen to sense the ECAP as it moves past, which in this example is electrode E8. Selection of an appropriate sense electrode can be determined by the ECAP algorithm 124a operable in the control circuitry 102 based on a number of factors. For example, it is preferable that a sense electrode S be sensibly chosen with respect to the active electrodes, such that the EM field produced around the active electrodes will dissipate (or more preferably, cease) at the sense electrode by the time the ECAP arrives. This simplifies ECAP detection at the sense electrode, because voltages present in the EM field will not interfere with and potentially mask the ECAP at the sense electrode. (Note that the stimulation artifact resulting from the EM field is not shown at the sense electrode in FIG. 8B for simplicity). To choose a sense electrode, the ECAP algorithm 124a preferably knows the pulse width of the pulses being issued, the extent of the size of the EM field (which can be estimated), the speed at which the ECAP is expected to travel, and the distance (x) between electrodes 16 in the electrode array 12, e.g., along a particular straight lead 14 or a paddle lead 15 (FIG. 1A).

In FIG. 8A for example, assume that the pulse width (of both phases of the biphasic pulses) is 0.1 ms as shown, and that sense electrode E8 is generally 2.0 cm away from the active electrodes (and hence their EM field). When the ECAP starts to form at time=0, it will arrive at electrode E8 after some delay 130 in accordance with the speed at which the ECAP moves (e.g., 5 cm/1 ms). In this example, the ECAP will start to pass sense electrode E8 at 0.4 ms. Thus, the ECAP algorithm 124a can thus enable sensing of the ECAP starting at or before time=0.4 ms after the start of the stimulation pulse. Such enabling can be controlled by controlling multiplexer 108 via bus 114 (FIG. 7) to pass the input from sense electrode E8 to a sense amp 110, an ADC 112, and ultimately the ECAP algorithm 124a. Sensing can last for as long as necessary to detect at least some aspects of the shape and size of the resulting ECAP. For example, sensing can last for a long enough time to allow the polarization and refraction peaks in the ECAP to be detected, which may comprise up to 3 ms for example. If the total duration of the ECAP is longer than the quite period between two subsequent pulses, e.g., between pulses 133a and 133b, subsequent pulses 133b may not be enabled until the ECAP measurement has finished.

Note that the ECAP algorithm 124a can enable measurement of an ECAP after a single pulse, or after a burst of (higher-frequency) pulses, such as is shown in FIG. 8B for electrode E3; E4 and E5 could also similarly comprise a burst of pulses, but this isn't shown for simplicity. If necessary, more than one ECAP can be measured after subsequent pulses or bursts and averaged to improve the fidelity of the signal. Further, pre-processing can occur prior to measuring the ECAP, as explained further below. Although FIGS. 8A and 8B show active electrodes and a sense electrode on a single lead 14, this is not required, and any active electrodes and sense electrodes can be chosen in an electrode array 12, including two-dimensional arrays provided by more than one lead 14, or on a single paddle lead 15 (FIG. 1A). The conductive case 30 (FIG. 1B) can also be used as a sensing electrode.

It is not strictly necessary that sensing occur at an electrode that would not experience interference from the EM field produced by the active electrodes, because masking techniques can be used to subtract voltages present in the EM field. Such masking techniques are described for example in M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamental sclinicalecapmeasuresin846); and I. Akhoun et al., "Electrically evoked compound action potential artifact rejection by independent component analysis: Technique validation," Hearing Research 302 pp. 60-73 (2013), which are both incorporated herein by reference. In fact, an active electrode can be used for ECAP sensing, which would involve quickly disconnecting the stimulation circuitry from the electrodes (e.g., at the switch matrix 106, FIG. 7) and quickly connecting the electrodes to the sensing circuitry (e.g., using MUX 108, FIG. 7).

The ECAP algorithm 124a could choose more than one electrode to act as a sense electrode. For example, ECAP algorithm 124a may sense the traveling ECAP at electrodes E6, E7, E8, E9, etc. This would require timing control, because E6 would sense before E7, etc., and might further require circuitry changes to accommodate sensing the ECAP at different electrodes at overlapping points in time. For example, each electrode might in this example require its own timing control (mux 108), and its own sense amp 110 and ADC 112, although this isn't illustrated in FIG. 7. Use of more than one sense electrode can be useful, as this allows the speed of the neural conduction to be calculated (if the electrode distance x is known). ECAP speed may indicate the types of neural fibers that are being recruited, which may in turn be useful to deciding how stimulation therapy in the IPG 100 (or ETS 170) might be adjusted, as explained further below.

A practical aspect that could affect sensing ECAPs in IPG 100 (or ETS 170) relates to passive charge recovery. As discussed earlier, the use of biphasic pulses are preferred in an IPG to actively recover charge during the second pulse phase that may have built up across capacitive elements (such as the DC blocking capacitors 107) during the first pulse phase. Because active charge recovery may not be perfect, IPG 100 may additionally include passive charge recovery as implemented by switches 122 shown in FIG. 7. Note that passive charge recovery can also be used following monophasic pulses. Passive charge recovery switches 122 are controlled by bus 120 issued from the control circuitry 102, and act to connect the inside plate of the DC blocking capacitors 107 to a common potential (Vref). When this occurs, the DC blocking capacitors 107 are connected in parallel between the common potential and the patient's tissue, which helps to equilibrate the charge across the capacitors and hence passively recover any remaining charge. Passive charge recovery using switches 122 typically occurs after the last phase of each stimulation pulse, as shown by the small, exponentially-decreasing waveforms 132 in FIG. 8B. Passive charge recovery might otherwise overlap in time with periods in which ECAP sensing is enabled. This could cause a problem for ECAP sensing, because it would place the common potential on the inputs to the multiplexer 108 that carry the ECAP signals. As a result, control circuitry 102 may wait to enable ECAP sensing until passive recovery (closing of switches 122) has finished. Alternatively, control circuitry 102 will preferably not close the passive recovery switch 122 associated with the sense electrode when an ECAP is to be sensed, although all other switches 122 may be closed. Once the ECAP has been sensed, control circuitry 102 may return to closing the sense electrode's switch 122 if desired.

As discussed earlier, it is important to determine a stimulation program that will best alleviate a patient's symptoms. Part of this "fitting" process includes determining which electrodes should be activated by the IPG 100 (or the ETS 170); the polarity of these active electrodes; the amplitude of stimulation; (if stimulation is issued in pulses) the pulse width, frequency, the duty cycle (DC), and shape of the waveform (e.g., pulses); etc. Initial fitting of a patient to determine a stimulation program that is effective usually occurs using a clinician programmer 90 (FIG. 3), but fitting or stimulation program adjustment can also occur using a patient external controller 50 (FIG. 2). Fitting can occur both during an external trial phase as described earlier and after a permanent IPG 100 has been implanted.

Of particular importance during fitting is determining an electrode configuration, i.e., the electrodes that should be active, their polarities, and the percentage of the total anodic or cathodic current that each active electrode will receive. The electrode configuration defines a Central Point of Stimulation (CPS) at a location in the patient's tissue, and one can be determined from the other: the CPS can be calculated using the electrode configuration, and a preset CPS can be used to calculate an appropriate electrode configuration centered at the CPS. CPS can be defined in different manners, as explained further below with reference to FIGS. 10A-10E.

Figure 9:
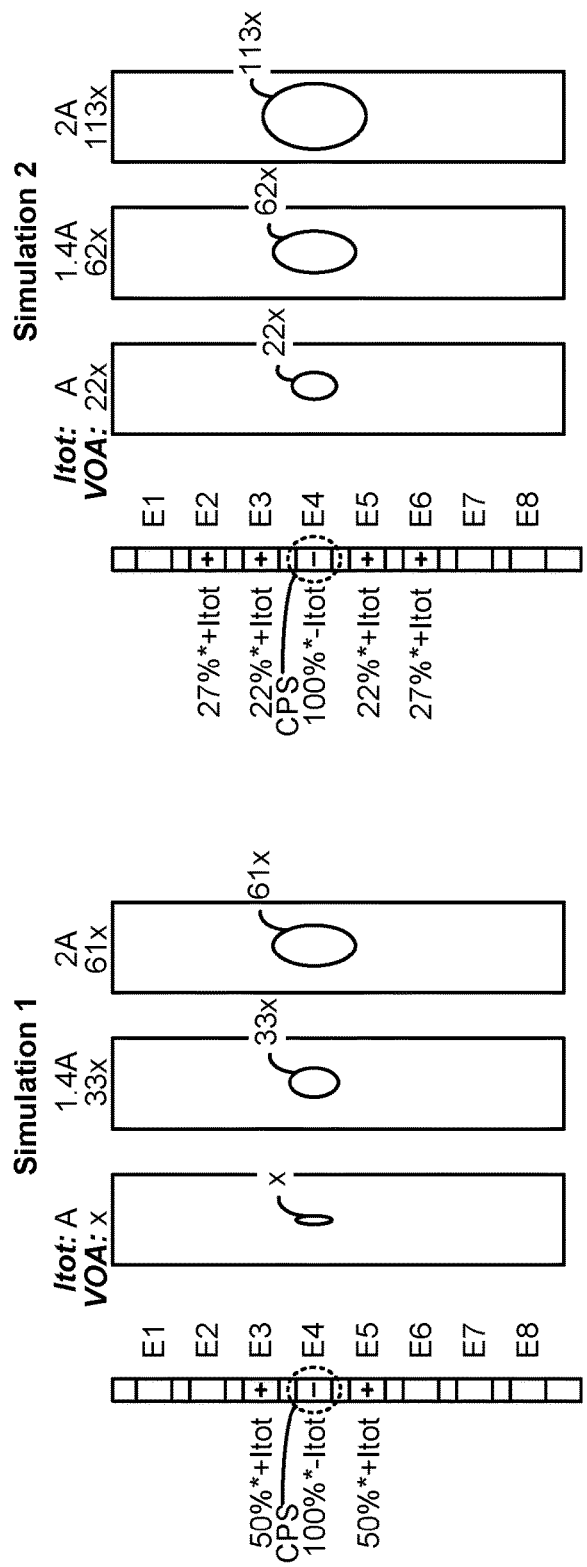
FIG. 9 shows the simulation of different electrodes configurations for the same Central Point of Stimulation (CPS), each showing expected volumes of recruited neural tissue.

FIG. 9 shows results of simulations in which the electrode configuration of a stimulation program is modified while keeping the location of the CPS constant. Three simulations are shown with different electrodes configurations, and each simulation shows results assuming different total anodic and cathodic current amplitudes, Itot.

Simulation 1 shows the tripolar stimulation program discussed earlier (FIG. 8B), in which electrode E4 is selected as a cathode electrode (providing 100% of the total cathodic current, −Itot), and flanking electrodes E3 and E5 are selected as anode electrodes (each providing 50% of the total anodic current, +Itot). Thus, the CPS is centered at electrode E4 in this example. Three different total anodic and cathodic amplitudes were simulated in this simulation: Itot=A, 1.4 A, and 2 A, where A is a generalized current magnitude that represents the minimum amplitude needed to produce elicit activation for the tripolar configuration used and according to the modeling algorithm used for the simulation environment. The simulation at each current amplitude allowed the EM field generated in the tissue to be calculated, which in turn allowed a number of recruited volume elements x to be determined, where x equals a minimum reference activation volume according to the modeling algorithm used for the simulation environment. At amplitude Itot=A, a single volume element x proximate to electrode E4 was recruited. As would be expected, higher current amplitudes create stronger EM fields, and thus recruit a greater number of volume elements. Thus, at amplitude Itot=1.4 A, 33x volume elements are recruited; at amplitude 2 A, 61x volume elements are recruited.

Simulation 2 adjusts the electrode configuration while keeping the CPS the same (centered at cathode electrode E4). In this example, additional anode electrodes (E2, E6) are activated, with anode electrodes E2, E3, E5, and E6 respectively providing 27%, 22%, 22%, and 27% of the total anodic current, +Itot. As seen, the different distribution of the anodic current affects the number of volume elements x expected to be recruited. At amplitude Itot=A, 22x volume elements are recruited; at amplitude 1.4 A, 62x volume elements are recruited; and at amplitude 2 A, 113x volume elements are recruited. Notice that the number of volume elements x recruited in Simulation 2 increases compared to Simulation 1 at the same current amplitudes due to the different electrode configuration used.

Simulation 3 also keeps the location of the CPS constant (centered at cathode electrode E4), but as compared to Simulation 1 changes the active anode electrodes to electrodes that are farther away from cathode E4. Specifically, electrodes E2 and E6 are selected as anode electrodes (each providing 50% of the total anodic current, +Itot). This different distribution of the anodic current also affects the number of volume elements x expected to be recruited. At amplitude Itot=A, 50x volume elements are recruited; at amplitude 1.4 A, 103x volume elements are recruited; and at amplitude 2 A, 156x volume elements are recruited. Notice that the number of volume elements x recruited in Simulation 3 increases compared to Simulations 1 and 2 at the same current amplitudes, again due to the different electrode configuration used.

These simulations indicate that useful adjustment to therapy—recruiting a larger or smaller number or neural fibers, and perhaps different types of fibers—can be made by adjusting the electrode configuration while keeping the location of the CPS constant. This is beneficial, because the CPS, once determined, is generally indicative of the location of a patient's symptoms (e.g., pain), and thus stimulation logically continues to be centered around that point.

There are different manners in which electrode configurations needed to achieve a desired location of the desired Central Point of Stimulation can be defined in three-dimensional space, some of which are shown in the examples of FIGS. 10A-10E. Although lead-based multi-polar stimulation is shown, monopolar stimulation—in which the case (30; FIG. 1B) is active and used as an electrode Ec—can also be used.

The CPS can comprise a midpoint between a (virtual) anode and a (virtual) cathode. FIG. 10A shows an example of bipolar stimulation as provided in FIG. 10A. As there is only one anode electrode E3 receiving all anodic current (100%*+Itot), the virtual anode Va corresponds to this electrode. Likewise, as there is only one cathode electrode E4 receiving all cathodic current (100*−Itot), the virtual cathode Vc corresponds to this electrode. The CPS can comprise a midpoint between the virtual anode and cathode Va and Vc, and thus is at a virtual position midway between E3 and E4. Note that designating E2 as a sole anode and E5 as a sole cathode (assuming a linear lead) would also comprise an electrode configuration centered at the same CPS position midway between E3 and E4.

In FIG. 10B, there are two cathode electrodes E3 and E4, with E3 providing 75% of the total cathodic current (75%*−Itot) and with E4 providing 25% (25%*−Itot). From this, a position of a virtual cathode (Vc) can be determined, which comprises a position between the cathode electrodes whose location is determined based upon the weighted relative amplitudes of the cathodes. For example, because the amplitude of E3 is three times as strong as the amplitude of E4, the virtual cathode Vc can be said to be located such that E4 is three times farther away from the Vc as is E3—i.e., Vc is located one-quarter of the distance from E3 to E4. (Note that other calculations can be used to determine the position of a virtual electrode). Notice that a virtual electrode (be it a virtual anode or cathode) may not reside at a position of a physical electrode. The virtual anode Va is at sole anode electrode E2. The CPS is again midway between Vc and Va as shown.

FIG. 10C shows a more complicated example having anodes and cathodes arrayed in two dimensions, such as could occur when two linear leads 14 are used, or when a paddle lead 15 is used (see FIG. 1A). Here, electrodes E3 and E11 are anodes, and split the total anodic current equally (50%*+Itot); because the relative weights are the same, the virtual anode Va is midway between them. Electrodes E4 and E12 comprise cathodes, with a 75%/25% split of the total cathodic current (−Itot). Thus, the virtual cathode Vc calculated as explained above is closer to E4, which positions the CPS generally at the center of the four electrodes, but slightly to the left as shown.

Other more-sophisticated techniques for defining CPS can involve analysis of the voltages or electric field (E=dV/dx) that would be expected at various locations in the patient's tissue given the electrode configuration. This may involve modeling the tissue environment in which the electrodes are placed, and may take into account the different conductivities and locations of specific tissues in that environment (such as the spinal cord, the cerebrospinal fluid (CSF) surrounding the spinal cord, vertebrae bone tissue, etc.).

FIG. 10D generically shows an EM field 99 around a group of electrodes chosen for stimulation, and defines the CPS as either the maximum voltage (Vmax), the maximum electric field (Emax), the minimum voltage (Vmin), or the minimum electric field (Emin). Either the maximum or the minimum voltage or electric field could be relevant, depending on the neural fibers one desires to recruit.

FIG. 10E defines the location of CPS as the center or centroid of the EM field 99 (Ecent). FIG. 10E also shows definition of CPS using an activation function, which is proportional to the second-order spatial derivative of the voltage ($\delta V2/\delta \times 2$); specifically CPS can be defined as the maximum of this derivative. This definition of CPS can be useful because large myelinated axons in the dorsal column are primarily aligned longitudinally along the spine, as explained in U.S. Patent Application Publication 2018/0056068.

In any of these examples for defining the position of the CPS, it should be noted that the CPS can be input, and then the electrode configuration computed (the electrodes that should be active, their polarities, and the percentage of the total anodic or cathodic current that each active electrode will receive. Conversely the CPS can be calculated from the electrode configuration that is specified. A clinician for example can enter an electrode configuration using the user interface of his clinician programmer 90, which can in turn calculate or determine CPS position in any of the ways specified in FIGS. 10A-10E. The clinician can also input a desired CPS position using the user interface, letting the clinician programmer automatically calculate one or more electrode configurations that arrive at this CPS position. An example of a system capable of deriving electrode configurations from a specified CPS position is described in "Precision Spectra™ System Programming Manual, Boston Scientific Corp., 90834018-18 Rev A (2016). Again, a CPS need not correspond to an actual physical electrode position.

Figure 11:
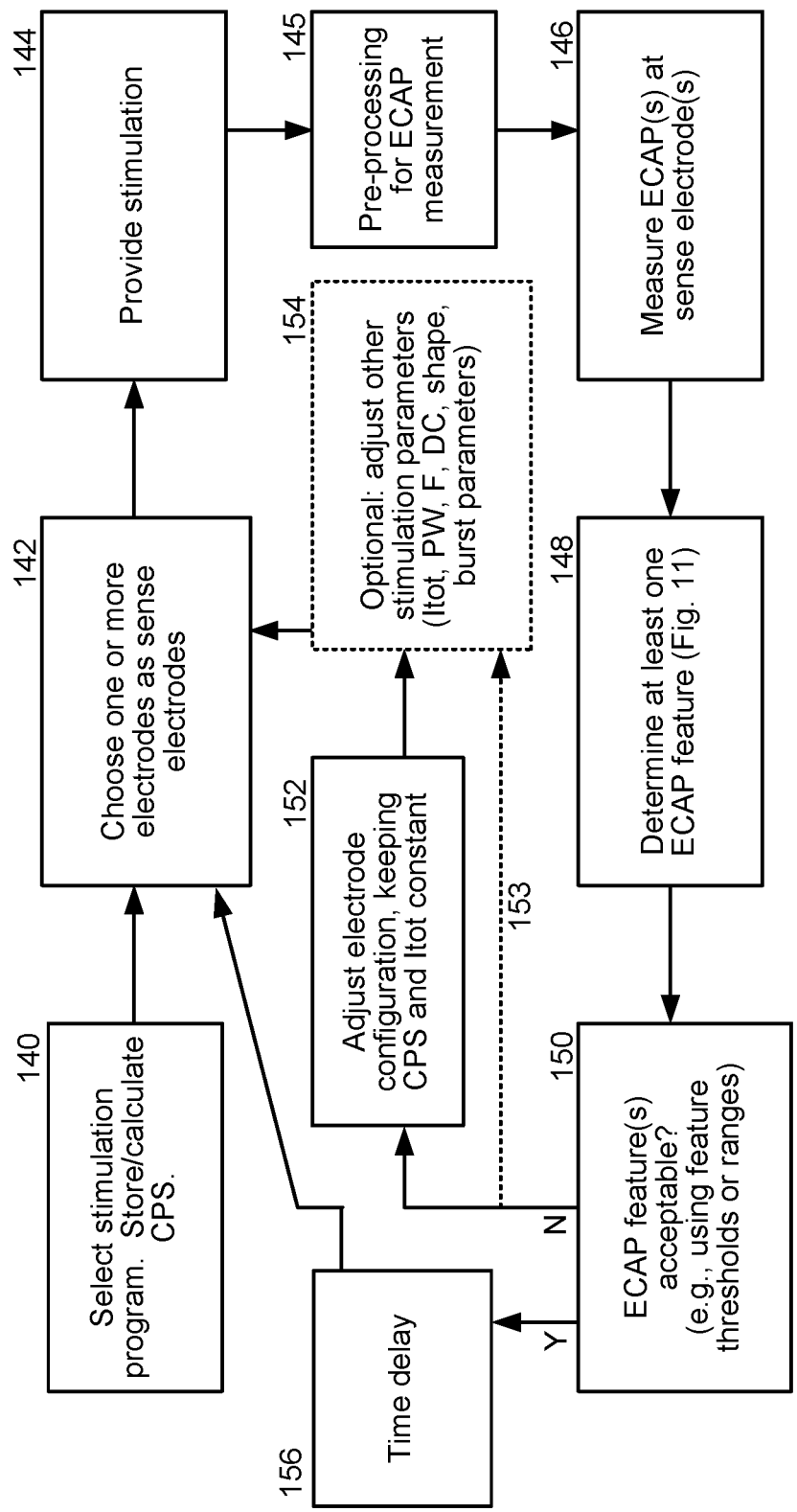
FIG. 11 shows a flow chart of an example of the ECAP algorithm operable solely in the IPG (or ETS) to adjust the electrode configuration of stimulation while keeping the location of the CPS constant.

In an actual implementation, the extent of neural recruitment can be determined by measuring the ECAP at the IPG 100 (or ETS 170), and ECAP algorithm 124a is useful in this regard. FIG. 11 shows an example of ECAP algorithm 124a that essentially operates exclusively in the IPG 100 (or ETS 170) to automatically adjust stimulation therapy. However, a portion of the ECAP algorithm may also be operable in an external programming device, such as the clinician programmer 90 or external controller 50 (FIGS. 2 and 3), as discussed later within respect to FIGS. 12A and 12B.

Prior to operation of the ECAP algorithm 124a in FIG. 11, a stimulation program is selected (step 140). Preferably, but not necessarily, the stimulation program is one that has been determined to be generally effective for the patient, but that may still benefit from adjustment. The stimulation program may be selected from a library of stimulation programs. The ECAP algorithm 124a may itself be used to generate the stimulation program. At this point the CPS is known or can be calculated based on the electrode configuration specified by the stimulation program, and is recorded. For example, the CPS may have been wirelessly provided to the IPG 100 (or ETS 170) by an external device such as the clinician programmer 90 or the external controller 50, and may have been transmitted to the IPG 100 (or ETS 170) with the stimulation program itself. Alternatively, the CPS can be calculated in the IPG 100 (or ETS 170) based upon the electrode configuration of the stimulation program, using any of the methods of FIGS. 10A-10E for example. Either way, the CPS is preferably stored in control circuitry 102 so that ECAP algorithm 124a can consult it later.

Once a stimulation program is chosen, the ECAP algorithm 124a can choose one or more electrodes to act as a sense electrode (S) (step 142), as described above. Stimulation can then be provided using the stimulation program (step 144). At this point, the algorithm may undertake certain pre-processing steps (145) in preparation for an upcoming ECAP measurement (146). Because the ECAP is generally a small voltage signal, it may be advisable for example to quantify any background "noise" inherent at the sense electrode so that it can be subtracted out of the ECAP measurement. Such noise may include background neural activity not related to the stimulation that the IPG 100 (or ETS 170) provides. Also, if sensing at the sense electrode occurs during a time when the EM fields related to stimulation have not dissipated, it can be advisable to quantify such stimulation artifacts at the sense electrode so that they may also be subtracted from the ECAP measurement.

Thereafter, ECAP algorithm 124a can measure one or more ECAPs at the sense electrode(s) (step 146) as described earlier. A plurality of ECAPs can be measured as explained above and averaged if necessary to improve the fidelity of the resulting signal.

Next, at least one ECAP feature is determined (step 148) from the measured ECAP(s) indicative of the size and shape of the ECAP. Various features for an ECAP are shown in FIG. 13. These include (but are not limited to):
a height of any peak (e.g., H_N1) present in the ECAP;
a peak-to-peak height between any two peaks (such as H_PtoP from N1 to P2);
a ratio of peak heights (e.g., H_N1/H_P2);
a peak width of any peak (e.g., the full width half maximum of a N1, FWHM_N1);
an area under any peak (e.g., A_N1);
a total area (A_tot) comprising the area under positive peaks with the area under negative peaks subtracted or added;
a length of any portion of the curve of the ECAP (e.g., the length of the curve from P1 to N2, L_P1toN2)
any time defining the duration of at least a portion of the ECAP (e.g., the time from P1 to N2, t_P1toN2);
a time delay from stimulation to issuance of the ECAP, which is indicative of the neural conduction speed of the ECAP, and which can be useful in discerning the types of neural fibers recruited;
any mathematical combination or function of these variables (e.g., H_N1/FWHM_N1 would generally specify a quality factor of peak N1).

Next the ECAP algorithm 124a assesses the one or more features of the ECAP to determine whether they are acceptable, which can include comparing the feature(s) to one or more thresholds or ranges (step 150). In this regard, the ECAP algorithm 124a is flexible, and what is deemed acceptable can vary depending on the circumstances. For example, at times it may be desirable that the ECAP have a large magnitude, such as H_N1 greater than a threshold, which might indicate a strong neural response effective for therapy. At other times, it may be desirable that the ECAP have a small magnitude not exceeding a threshold, which might indicate that the neural tissue is not being overstimulated. Alternatively, an ECAP can be deemed acceptable if one or more of its features hasn't changed significantly (is within a range) compared to past ECAP measurements; this might indicate that the patient is receiving the desired amount of neural recruitment, and that neural recruitment isn't being affected by variances such as patient movement, scarring of tissue, etc. ECAP features can be indicative of the neural fibers that are recruited, and thus acceptable thresholds or ranges may be set so as to active activate or inhibit different fibers.

Step 150 can also be used to calibrate the algorithm 124a, and in particular can be used to determine which the types of stimulation adjustments that have had a marked effect on the sensed ECAP, which can in turn adjust the manner in which the ECAP algorithm iteratively operates as it learns which adjustments the ECAPs are sensitive to. This can also involve assessing the sensitivity of various ECAP features. For example, assume that adjusting from a first electrode configuration (such as shown in Simulation 1 in FIG. 9) to a second electrode configuration (Simulation 2) gives rise to a large change in a particular ECAP feature such as the height of peak N1 (H_N1), but only a small change in its width (FWHM_N1). This might suggest to the algorithm 124a that in later iterations it should adjust to a third electrode configuration (Simulation 3) but that it will thereafter only assess the peak height that was shown earlier to be sensitive to the adjustment. Determining a sensitive feature of the ECAP can also help in choosing a new electrode configuration, such as by varying the anode percentages in Simulation 2.

Moreover, and as explained further below, the ECAP algorithm 124a may at least for some iterations change stimulation parameters other than the electrode configuration—such as Itot, pulse width, frequency, duty cycle, waveform shape, various burst parameters, etc. (see step 154). Should adjustment of one of those parameters significantly change a particular ECAP feature—i.e., that feature is sensitive to the changed parameter—the ECAP algorithm 124a may in future iterations focus on adjusting that parameters and ignoring adjustment of others parameters to which the ECAP is less sensitive. In short, the ECAP algorithm 124a has the capability to learn and to change its operation and what it adjusts based on the sensitivity of the ECAP feature(s) it determines. Patient feedback—whether adjustments are helping the patient's symptoms or creating unwanted side effects—in addition to the sensed ECAPs can also be useful to algorithm learning.

If the ECAP feature(s) are acceptable, the ECAP algorithm 124a can eventually repeat, perhaps after a time delay (step 156) such as every minute or so, to allow the algorithm to gradually adjust the stimulation program the IPG 100 (or ETS 170) is running, as discussed next.

If the ECAP feature(s) are not acceptable (150), the ECAP algorithm 124a can adjust the electrode configuration—the active electrodes, their polarities, and relative amplitudes—of the stimulation program while keeping the location of the Central Point of Stimulation (CPS) constant (step 152). As explained earlier, this can involve choosing new (FIG. 9, Simulation 3, compared to Simulation 1) or additional (FIG. 9, Simulation 2, compared to Simulation 1) electrodes for stimulation. As noted earlier, and as simulation shows (FIG. 9), such an adjustment is logical as it can affect the volume of recruited neural fibers without changing the basic physical location at which stimulation occurs. Such changes in recruited volume (or change in recruited neural fibers more generally), should warrant a change in the resulting ECAP, which can be verified by iterative use of the ECAP algorithm 124a. It is preferred that adjusting the electrode configuration at this step does not change the total anodic and cathode current amplitude, Itot, although of course the percentage in which those total currents are be divided between the electrodes can vary. It is further preferred that the pulse width, frequency, duty cycle (DC), and stimulation waveform shape, and other stimulation parameters not change, so that the stimulation program and the adjusted stimulation program comprise the same energy.

However, if desired, other stimulation parameters can also be adjusted in addition to the electrode configuration, as set forth in optional step 154. For example, the pulse width of the pulses (PW), the frequency of the pulses (F), the duty cycle (DC), the waveform shape, and various burst parameters (such as number and duration of pulses) can be changed. However, it is preferred for at least some iterations of the ECAP algorithm 124a that these other stimulation parameters remain constant, so that only the effect of the change of the electrode configuration on the ECAP (152) can be analyzed in subsequent steps. It should be noted that these other stimulation parameters can be changed outside of the use of ECAP algorithm 124a; for example, they may be changed when selecting the stimulation program (140) prior to beginning execution of the ECAP algorithm 124a. Furthermore, there may be other reasons not related to ECAP generation or detection that warrant changing of stimulation parameters. For one, the patient or clinician using their external devices 50 or 90 may simply desire to change the amplitude of simulation or other pulse parameters.

The total anodic and cathodic current amplitude Itot can also be changed at optional step 154, although again it is preferred for at least some iterations of the ECAP algorithm 124a that Itot remain constant, so that only the effect of the change of the electrode configuration on the ECAP (152) can be analyzed in subsequent steps. Nonetheless, the utility of adjusting Itot is suggested as reasonable in the simulations of FIG. 9. For example, notice that Simulation 1 at Itot=2 A and a first electrode configuration recruits approximately the same volume (61x) as does Simulation 2 at Itot=1.4 A and at a second electrode configuration (62x). Adjusting between these values of Itot may be worth trying because while they are forecasted to recruit approximately the same volumes, the types of fibers, and hence the ECAPs they generate, might differ.

If ECAP feature(s) are not acceptable (150), it is not necessary that every iteration of ECAP algorithm 124a adjust the electrode configuration (152). As shown by optional path 153, the algorithm may sometimes proceed to optional step 154 to allow other stimulation parameters to be adjusted, as discussed above.

After adjustment, the ECAP algorithm 124a largely repeats—which will involve for at least some iterations applying stimulation with new electrode configurations, and measuring the resulting ECAP to see if the ECAP feature(s) are can be rendered acceptable. While it would be expected that the sense electrode(s) chosen earlier would remain the same, they could be adjusted (142). This could be sensible in case the new electrode configuration chosen places newly-active electrodes too close to the sense electrode(s) picked earlier.

Figure 12A:
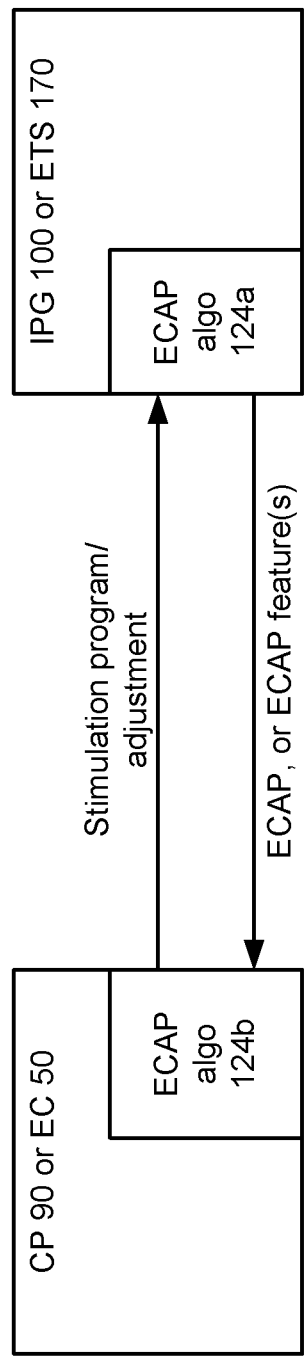
FIGS. 12A and 12B show examples of ECAP algorithms operable in the IPG (or ETS) and an external device for programming the IPG (or ETS), wherein the algorithms operate to adjust the electrode configuration of stimulation while keeping the location of the CPS constant.

As noted above, the ECAP algorithm can alternatively operate with the assistance of external devices, as shown in FIG. 12A, which shows an external programming device (such as the clinician programmer 90 or external controller 50) in wireless communication with the IPG 100 (or ETS 170). In this example, an ECAP algorithm 124b is included in the external device, which can receive information from the IPG 100 (or ETS 170) regarding the ECAPs it measures, process the ECAP, and send a stimulation program (or adjustment) to the IPG. ECAP algorithm 124a again operates in the IPG 100 (or ETS 170), but in this example off-loads ECAP analysis and stimulation program adjustment to ECAP algorithm 124b in the external device. A system as shown in FIG. 12A is particularly useful when fitting the implant patient, i.e., when determining a stimulation program that would be useful in treating the patient's symptoms.

Figure 12B:
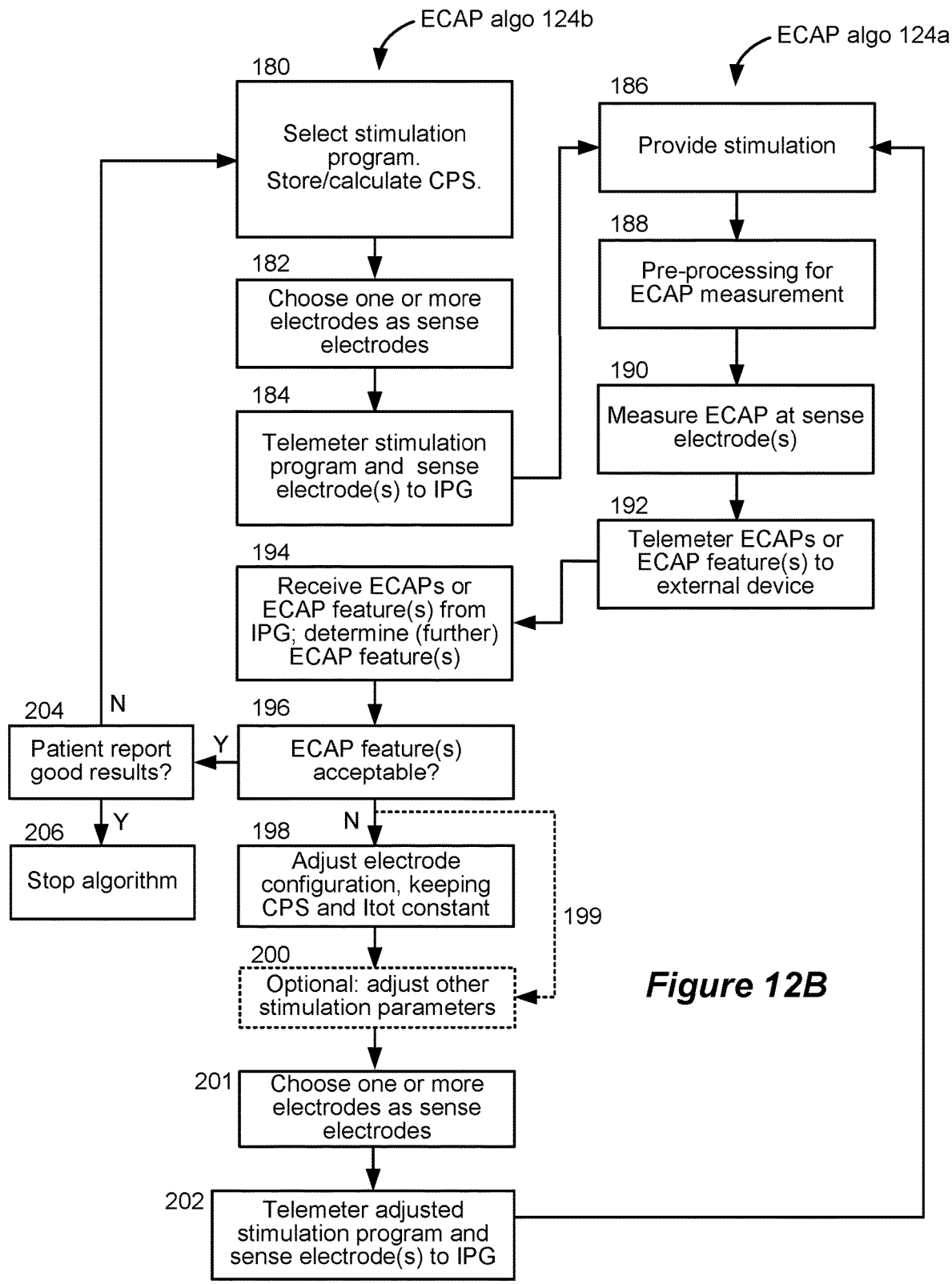

FIG. 12B shows ECAP algorithms 124a and 124b in flow chart form. As before, the algorithms start with a stimulation program, which may be entered by the clinician or patient using the user interfaces of external devices 90 or 50, or which may have been determined in some other manner. CPS for the stimulation program is stored at the external device (180), and can be calculated if not entered directly, as described earlier. Next, one or more sense electrodes can be chosen at the external device (182). This can occur automatically given the particulars of the stimulation program (as occurred in the IPG 100; FIG. 10, step 142), or the clinician can choose sense electrode(s) that are reasonable given the electrodes at which stimulation is occurring using the user interface of the external device. The stimulation program and sense electrode information is then telemetered to the IPG 100 (or ETS 170) (184), where ECAP algorithm 124a takes over.

The ECAP algorithm 124a in the IPG 100 (or ETS 170) next performs many of the same steps described earlier, such as executing the stimulation program (186); pre-processing for the upcoming ECAP measurement (188); and measuring the ECAP(s) at the prescribed sense electrode(s) (190). At this point (192), the ECAP algorithm 124a will telemeter at least some information regarding the measured ECAP(s) from the IPG 100 (or ETS 170) to the external device (to algorithm 124b). For example, the entire ECAP waveform(s) can be telemetered (e.g., preferably after being digitized; see ADCs 112, FIG. 7). Alternatively, the ECAP algorithm 124a may determine the ECAP feature(s) as before, and telemeter those feature(s) to the external device.

Once at received at the external device, ECAP algorithm 124b will process the received ECAP information as necessary (194). For example, the ECAP feature(s) can now be determined from the telemetered waveform information, or even further ECAP features can be determined if desired. Then, acceptability of the ECAP feature(s) are determined as described earlier (196). If the features are acceptable, and assuming the patient reports good therapeutic result (204), the ECAP algorithm 124b can terminate. (ECAP algorithm 124a can continue to run in the IPG 100 (or ETS 170) as described earlier in FIG. 11 to automatically adjust therapy if desired). If the patient does not report good results, the algorithm can start over with selection of a new stimulation program (180).

If the ECAP feature(s) are not acceptable (196), ECAP algorithm 124b can as before adjust the electrode configuration of the stimulation program, preferably keeping for at least some iterations of the algorithm the CPS (recorded earlier) and total anodic and cathodic current Itot constant (198). This adjustment can occur automatically at the external device, or may involve clinician input. As before, other stimulation parameters can optionally be adjusted (199, 200). Once the stimulation program has been so adjusted, the sense electrode(s) can be adjusted if necessary (201), and then the adjusted stimulation program (and adjusted sense electrode(s) information if necessary) is telemetered to the IPG 100 (or ETS 170) (202), where the adjusted stimulation program is then executed (ECAP algorithm 124a). ECAP measurements can be taken again, with results telemetered to the external device to see if the adjustment has rendered ECAP feature(s) that are now acceptable.

Figure 14:
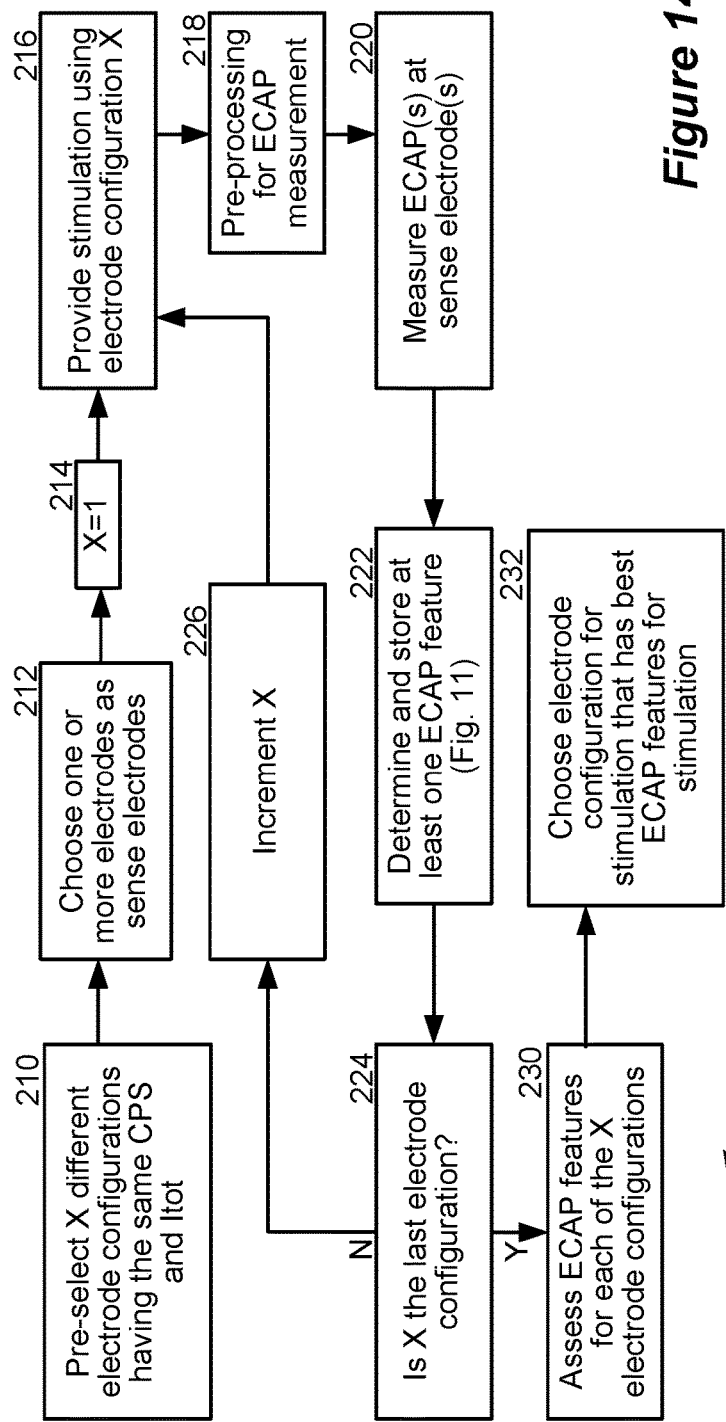
FIG. 14 shows another example of ECAP algorithm which involves testing preset electrode configurations.
Figure 14:
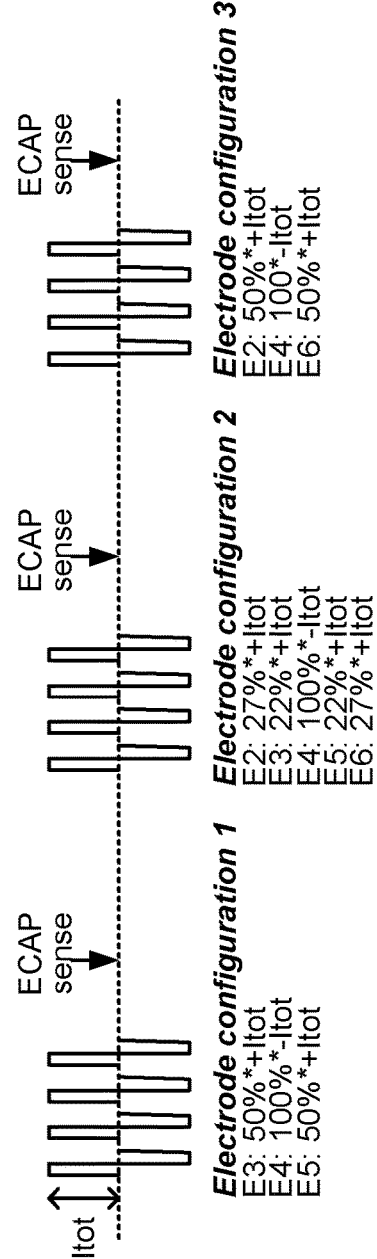

FIG. 14 shows another example of ECAP algorithm 124a operable in the IPG 100 (or ETS 170). This could however be expanded to include use of ECAP algorithm 124b in an external device, such as occurred in FIG. 12B, although this alternative is not depicted for brevity.

In this example of ECAP algorithm 124a, X different electrode configurations creating stimulation located at a constant CPS and with a constant total anodic and cathodic current amplitude Itot are pre-selected (210). As explained further below, each are tried in succession to determine which results in most favorable ECAP feature(s). The X different electrode configurations can be selected in any number of ways: they may be automatically generated by the external device or the IPG 100 (or ETS 170) once the CPS and Itot are known, or the clinician for example can manually specify the electrode configurations at the external device. In just one example the three different electrode configurations depicted in Simulations 1-3 in FIG. 9 could be used. These electrode configurations are shown at the bottom of FIG. 14, and further shows that the ECAPs in this example are sensed following a burst of pulses specified by the electrode configurations.

One or more sense electrodes are chosen as before (212), and X is set to 1 (214), selecting electrode configuration 1, which is used to provide stimulation (216). Pre-processing prior to an ECAP measurement can be performed as described earlier (218), and one or more ECAPs produced by the electrode configuration 1 are measured at the sense electrode(s) (220). One or more features for the ECAP(s) are determined and stored (222). If this electrode configuration is not the last electrode configuration to be tested (224), X is incremented (226), effectively selecting electrode configuration 2, which is tested next. Once all X electrode configurations have been tested (224), the previously-stored ECAP feature(s) for each of the electrode configurations are assessed (230), and the electrode configuration having the best ECAP feature(s) is chosen for stimulation (232).

One skilled in the art will understand that the ECAP algorithm 124a and 124b and/or any supporting user interface program will comprise instructions that can be stored on non-transitory machine-readable media, such as magnetic, optical, or solid-state memories. Such memories may be within the IPG or ETS itself (i.e., stored in association with control circuitry 102), within the external system (e.g., 50 or 90), or readable by the external system (e.g., memory sticks or disks). Such memories may also include those within Internet or other network servers, such as an implantable medical device manufacturer's server or an app store server, which may be downloaded to the external system.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A medical device, comprising:
a plurality of electrodes each configured to be electrically coupled in contact with a patient's tissue; and
control circuitry configured to
control stimulation circuitry to issue a stimulation waveform pursuant to an stimulation program, wherein the stimulation program comprises a first electrode configuration,
wherein the first electrode configuration defines which of the plurality of electrodes should be active, whether each active electrode comprises an anode electrode or a cathode electrode, and a percentage of a first total anodic current for each active anode electrode and a percentage of a first cathodic current for each active cathode electrode,
wherein the first electrode configuration is associated with a center point of stimulation (CPS) in a patient's tissue,
determine a neural response to the stimulation waveform at at least one electrode of the plurality of electrodes and to determine at least one feature of the neural response, and
based on the at least one feature, adjust the stimulation program so that it comprises a second electrode configuration different from the first electrode configuration, wherein the second electrode configuration is associated with a CPS in the patient's tissue that equals the CPS associated with the first electrode configuration.

2. The device of claim 1, wherein the neural response comprises an Evoked Compound Action Potential (ECAP).

3. The device of claim 2, wherein the at least one feature is indicative of the shape and/or size of the ECAP.

4. The device of claim 3, wherein the at least one feature comprises an ECAP peak height or width.

5. The device of claim 3, wherein the at least one feature comprises an area of the ECAP or of any ECAP peak.

6. The device of claim 3, wherein the at least one feature comprises a length of any portion of the ECAP.

7. The device of claim 2, wherein the at least one feature comprises a time defining a duration of any portion of the ECAP, or a time delay from stimulation to issuance of the ECAP.

8. The device of claim 1, wherein the control circuitry determines the at least one feature of the neural response by comparing the at least one feature to at least one threshold or range.

9. The device of claim 1, wherein the control circuitry determines the neural response to the stimulation waveform at at least one non-active electrode of the plurality of electrodes.

10. The device of claim 9, wherein the control circuitry is further configured to automatically select the at least one non-active electrode.

11. The device of claim 1, wherein the control circuitry further comprises at least one amplifier configured to amplify the neural response at the at least one electrode.

12. The device of claim 11, wherein the control circuitry further comprises at least one Analog-to-Digital converter configured to receive the output of the at least one amplifier and to digitize the amplified neural response.

13. The device of claim 1, wherein a second total anodic current and a second total cathodic current of the second electrode configuration respectively equal the first total anodic current and first total cathodic current of the first electrode configuration.

14. The device of claim 1, wherein the stimulation program comprises a pulse width, frequency, duty cycle, and waveform shape, and wherein the adjusted stimulation program comprises the same pulse width, frequency, duty cycle and waveform shape as the stimulation program.

15. The device of claim 1, wherein the stimulation program comprises a pulse width, frequency, duty cycle, and waveform shape, and wherein one or more of the pulse width, frequency, duty cycle or waveform shape of the adjusted stimulation program are different from the stimulation program.

16. The device of claim 1, wherein the stimulation program and the adjusted stimulation program comprise the same energy.

17. The device of claim 1, further comprising a case for holding the control circuitry, wherein the medical device comprises an implantable pulse generator and the case is configured for implantation in a patient's tissue.

18. The device of claim 17, wherein the case comprises either one of the active electrodes, or one of the at least one electrodes at which the neural response is detected.

19. The device of claim 1, further comprising a housing for holding the control circuitry, wherein the medical device comprises an external stimulator and the housing is not configured for implantation in a patient's tissue.

20. The device of claim 1, wherein the electrodes are located on one or more electrode leads.

* * * * *